US00PP31744P3

(12) United States Plant Patent

Maillard et al.

(10) Patent No.: US PP31,744 P3

(45) Date of Patent: May 12, 2020

(54) NECTARINE TREE NAMED 'NSRED15273'

(50) Latin Name: ***Prunus persica* (L.) Batsch**
Varietal Denomination: NSRED15273

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,465

(22) Filed: Nov. 20, 2018

(65) Prior Publication Data

US 2019/0159386 P1 May 23, 2019

(30) Foreign Application Priority Data

Nov. 23, 2017 (QZ) ..... PBR 2017/3059

(51) Int. Cl.
*A01H 5/08* (2018.01)
*A01H 6/74* (2018.01)

(52) U.S. Cl.
USPC ..... Plt./187
CPC ..... *A01H 6/7454* (2018.05)

(58) Field of Classification Search
USPC ..... Plt./187
See application file for complete search history.

*Primary Examiner* — Anne Marie Grunberg

(74) *Attorney, Agent, or Firm* — Birch, Stewart, Kolasch & Birch, LLP

(57) ABSTRACT

A new and distinct variety of red blood nectarine tree denominated 'NSRED15273' has fruits with high eating quality and very long shelf life without alteration before and after harvesting, with a semi-sweet pink red blood colored flesh, and a very high percentage of purple red blush on skin surface.

3 Drawing Sheets

Botanical classification: *Prunus persica* (L.) Batsch.

Variety denomination: 'NSRED15273'.

This application claims priority of Community plant variety right No. 2017/3059 filed on Nov. 23, 2017 (Nov. 23, 2017) which is hereby incorporated by reference in its entirety.

The new variety named 'NSRED15273' is also known as 26.30.93.15NS-ASF15273. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'NSRED15273', the provisional reference of this white flat nectarine tree variety was 26.30.93.15NS, corresponding to the tree 93 located in line 30 of the parcel 26 and selected during the year 2015. The letters "NS" are related to the first letters of the type of tree in French (NS for "Nectarine Sanguine", that means "blood nectarine"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'NSRED15273', the clone reference was 'ASF15273'.

BACKGROUND OF THE NEW VARIETY

The present invention relates to a new and distinct variety of blood nectarine tree, also named red colored flesh nectarine, *Prunus persica* (L.) Batsch, which has been given the variety denomination 'NSRED15273'. This new tree produces fruits with a long shelf life without alteration both on the tree after growth completion and after harvesting, very good eating quality, clingstone dark red or blood red flesh fruits for fresh market in August in the Pyrénées-Orientales department, France. Contrast is made to 'NECTARPERF' white nectarine tree (U.S. Plant Pat. No. 23,357) to 'NSRED14262' blood nectarine tree (U.S. Plant patent application Ser. No. 16/350,460) and to 'NSRED15270' blood nectarine tree (U.S. Plant patent application Ser. No. 16/350,466) for reliable description. 'NSRED15273' is a promising candidate for commercial success in that it has very attractive fruits with very long shelf life without alteration both before and after harvesting.

ORIGIN OF THE VARIETY

The 'NSRED15273' red nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 700 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'NSRED15273' variety resulted from an open pollination of the 'NECTARPERF' white nectarine tree (U.S. Plant Pat. No. 23,357), which was used as the seed parent. Then, the pollen parent of the new variety 'NSRED15273' remains unknown.

The 'NSRED15273' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NSRED15273' red nectarine tree blooms during March near Elne in the Pyrénées-Orientales department, France. More particularly, it usually blooms between March $7^{th}$ and March $20^{th}$. The blooming period is considered medium. However, it was observed that its date of blooming seems to be highly dependant on climatic conditions.

The first fruit of 'NSRED15273' ripens late in the season, generally at the beginning of August or mid-August. More particularly, it usually ripens between August $5^{th}$ and August $24^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
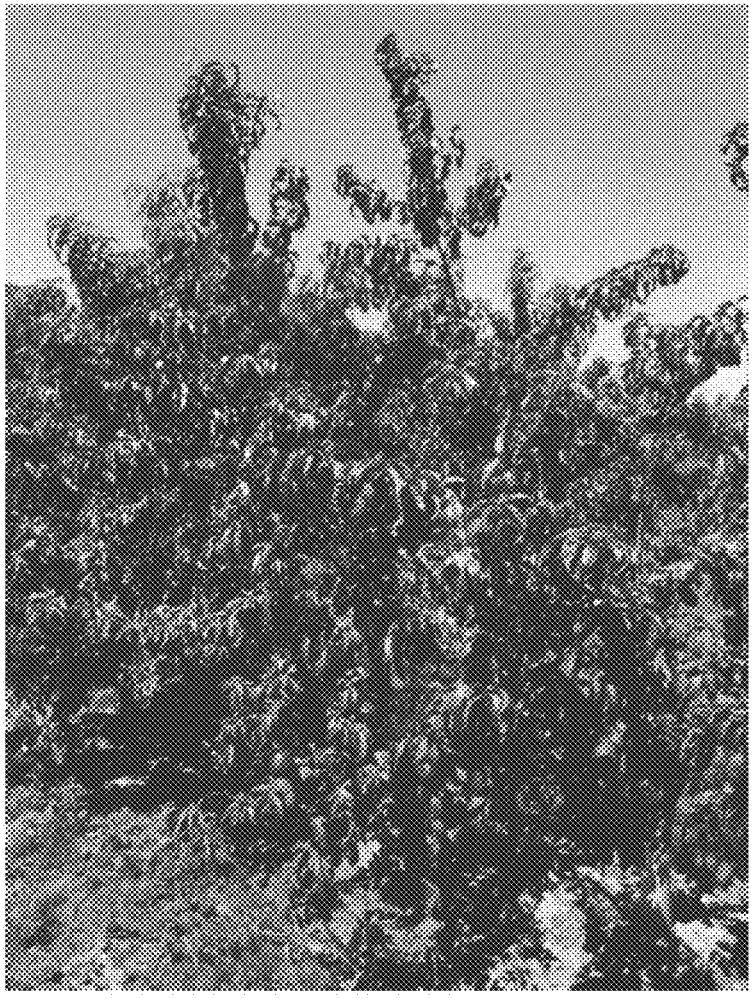
FIG. 1 is a color photograph which shows a view of a tree of the new variety in orchard, with branches bearing fruits.
Figure 2:
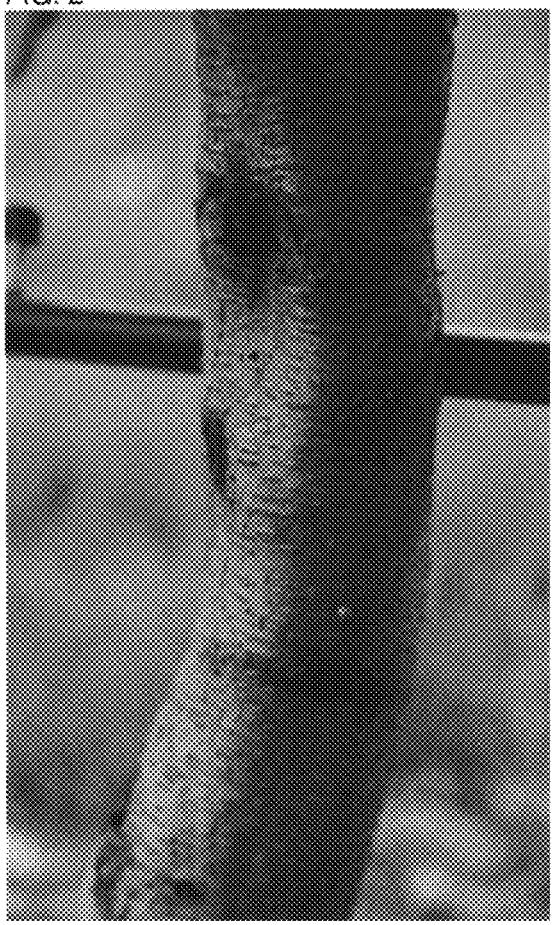
FIG. 2 is a color photograph which shows a close view of the trunk of a typical tree of the new variety 'NSRED15273' in orchard.
Figure 3:
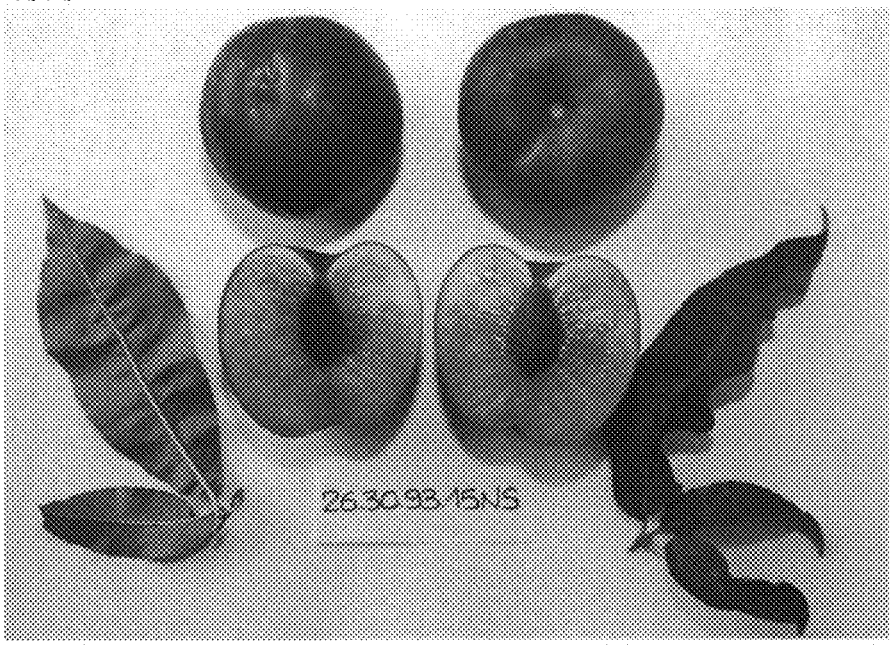
FIG. 3 is a color photograph which shows the upper and lower sides of leaves of the variety and three typical specimens of the fruit, one having been cut in halves with the stone being left into one of the halves for depicting fruit flesh stone and stone cavity of the new variety, also referenced as 26.30.93.15NS on FIG. 3.
Figure 4:
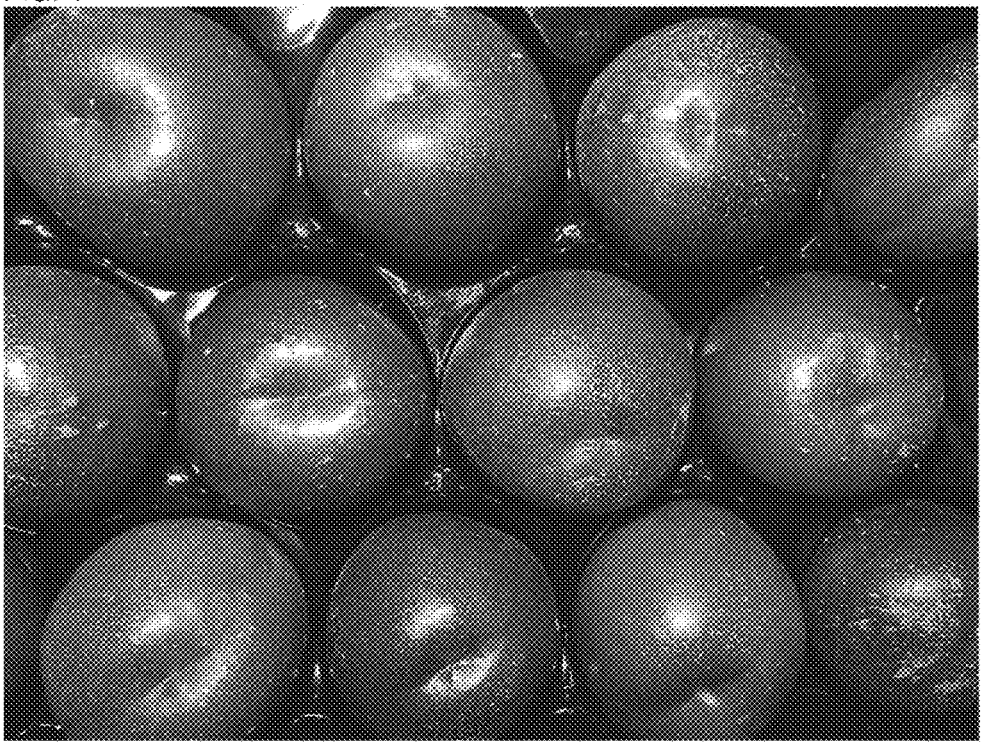
FIG. 4 is a color photograph that shows a close view of typical fruits of the new variety 'NSRED15273' at ripening time
Figure 5:
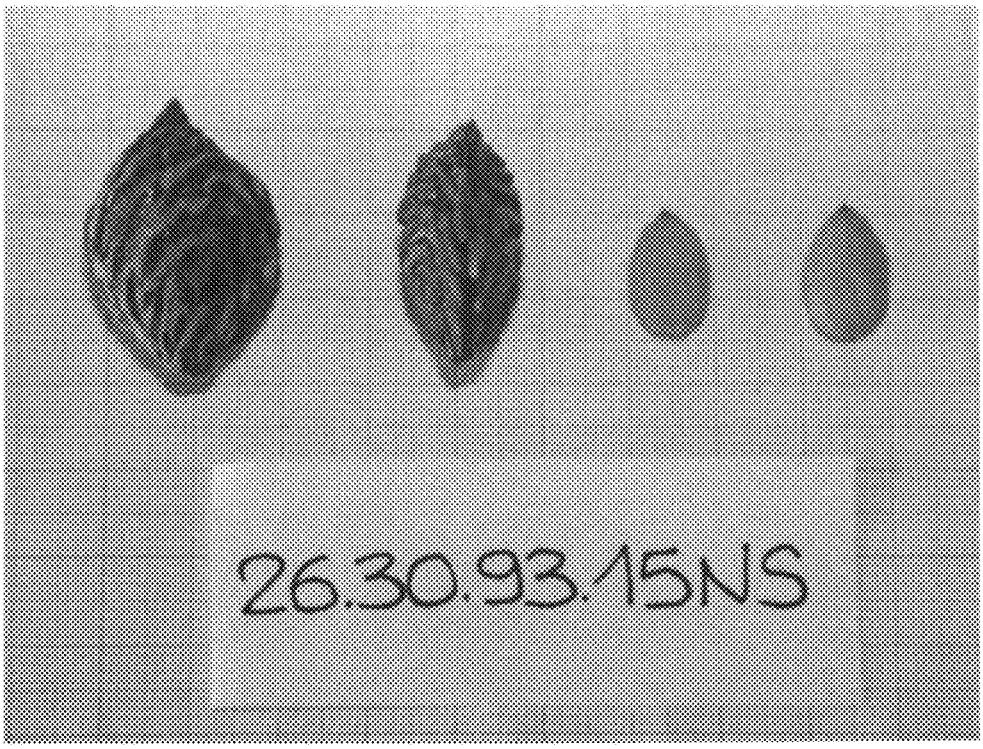
FIG. 5 is a color photograph that show different views of the stone and the kernel of the stone of the new variety, also referenced as 26.30.93.15NS on FIG. 5.

The views of trees and trunk have been photographed in their third growing season (second year of production). The views of fruits, leaves and stones have been photographed in their second growing season (first year of production).

Due to chemical development, processing and printing, the leaves and fruit depicted in these photographs may or may not be accurate when compared to the actual botanical specimen.

DETAILED BOTANICAL DESCRIPTION

The trees, leaves, fruits and stone may vary in slight detail due to variations in soil type, cultural practices, and climatic condition. The potential for commercial production of fresh fruits by 'NSRED15273' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered medium; the flowering usually begins during the first two weeks of March. The type of flower is showy (rosette). Leaf glands are present and round. The fruit flesh is pink red, also named blood red, and sometimes darker around the stone cavity. The fruit skin is medium thick, with a homogenous purple red color on a purple background. The stone is clingstone, and his size is medium. Fruit taste is semi-sweet, very aromatic and with a high level of sugars.

Compared to 'NECTARPERF' white nectarine tree (U.S. Plant Pat. No. 23,357), which is the seed parent of 'NSRED15273', the new variety shows a surprising bright blood pink red flesh color whereas the fruits of 'NECTARPERF' present a white colored flesh.

The ripening time of the new variety 'NSRED15273' is considered late, namely early in August or at the middle of the month, whereas the fruits of the variety 'NECTARPERF' ripen later during the season, namely at the end of August or early in September depending on the years.

Moreover, the leaf glands of the new variety 'NSRED15273' are round in shape, whereas the leaf glands of the seed variety 'NECTARPERF' are reniform.

Compared to 'NSRED14262' blood nectarine tree (U.S. Plant patent application Ser. No. 16/350,460), the fruits of the variety 'NSRED15273' ripen later. The similar variety named 'NSRED14262' produces smaller fruits than those of the new variety 'NSRED15273'. Consequently, the fruits produced by the new variety 'NSRED15273' are heavier than the fruits of the variety 'NSRED14262'.

The fruit skin color of the new variety 'NSRED15273' is also considered darker than fruit skin color of the similar variety 'NSRED14262'.

Compared to 'NSRED15270' blood nectarine tree (U.S. Plant patent application Ser. No. 16/350,466), the new variety 'NSRED15273' ripens approximately at the same period. These two varieties are different considered their respective taste. Indeed, the fruit taste for the new variety 'NSRED15273' is considered semi-sweet, whereas the fruits of the similar variety 'NSRED15270' have a taste which is considered equilibrate. The aromas are more pronounced in the flavor of the new variety 'NSRED15273'. The fruit skin of similar variety 'NSRED15270' presents some very thin lenticels, smaller than the lenticels of the fruit skin of the new variety 'NSRED15273', which are considered thin.

DETAILED DESCRIPTION

Referring more specifically to the pomological details of this new and distinct variety of red nectarine tree, the following was observed on trees in their second growing season (first year of production) for fruits, leaves and stones and on trees in their third growing season (second year of production) for the trees and trunk, under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. (Royal Horticultural Society) Colour Chart (Fourth Edition) provided by The Royal Horticultural Society of Great Britain.

Tree:

*Size.*—

*Generally.*—Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm including current season shoots length. The tree size is consistently reduces to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium vigorous.

*Productivity.*—The productivity is considered good and regular, every year. Fruit set is spaced by thinning to develop the remaining fruit into the desired market sized fruit. The number of the fruit set varies with the prevailing climatic conditions and cultural practices employed during the bloom period and is therefore not distinctive of the present variety.

*Bearer.*—Very regular. The fruit distribution is considered homogenous on mixed branches and spurs having more than 1 year. Thinning of 1 fruit out of 3 was necessary for the tree valorisation. Thinning was necessary every year during the years of observation.

*Form.*—The 'NSRED15273' variety has naturally a semi-flared to semi-upright shape.

*Density.*—Considered dense.

*Hardiness.*—The present tree was grown and evaluated in France. The variety appears to be hardy under the central Pyrénées-Orientales departement typical climatic conditions. Experimentations on the same orchard in Elne, Pyrénées-Orienteles department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017 and 1017 hours in 2017-2018 showed a good behaviour of the trees in all cases. No damages were caused by ascertained temperatures as low as −12 degrees Celsius in winter. The tree was also very resistant to frosty springtime weather.

Trunk:

*Diameter.*—Approximately 74.0 to 84.0 millimeters in diameter when measured at a distance of approximately 20.0 centimeters above the soil level.

*Bark texture.*—Considered rough, with lenticels.

*Lenticels.*—Numerous lenticels are present. The number of lenticels reaches 3 lenticels per $cm^2$. The lenticels range in size approximately 1.5 to 2.0 millimeters in height and from approximately 5.0 to 6.5 millimeters in width.

*Lenticel color.*—The lenticels have a light orange color (RHS Greyed Orange 164 A).

*Bark coloration.*—The bark has a brown (RHS Greyed Orange 165 A) color.

Branches:

*Size.*—Mature branches and current season shoots are considered medium for the variety.

*Diameter.*—Average as compared to other nectarine varieties. The current season shoots have a diameter of approximately 4.0 to 6.0 millimeters, and branches in their second growing season have a diameter from 8.0 to 10.0 millimeters.

*Surface texture.*—Average, wood which is several years old has no furrowed appearance.

*Crotch angles.*—Primary branches are considered variable, but the crotch angles are generally of 45 degrees for the current season shoots and 80 degrees for the mature branches, from the horizontal axis. This particular characteristic is not considered distinctive of the variety, however.

*Internode length.*—Generally between 20.0 and 22.0 millimeters for the current season shoots and between 31.0 and 36.0 millimeters for the mature branches.

*Current seasons shoots.*—

*Color.*—The color of new shoot tips is considered green (RHS Yellow Green 145 A) on lower part of new shoot tips, whereas the upper part is darker and colored in purple (RHS Greyed Red 178 A).

*Surface texture.*—Smooth, without lenticel.

*Mature branches.*—

*Color of mature branches.*—Light brown (RHS Grey Brown 199 A).

*Surface texture.*—The surface texture of mature branches is rough, with small lenticels.

*Lenticels.*—The number of lenticels on mature branches reaches 3 lenticels per $cm^2$. The lenticels range in size approximately 1.0 to 1.5 millimeters in height and approximately 1.5 to 2.5 millimeters in width. The lenticels are stretched round in shape.

*Lenticel color.*—The lenticels on mature branches have a beige color (RHS Greyed Orange 165 D).

Leaves:

*Size.*—Considered medium for the species. The ratio between the leaf length and the leaf width is 3.36.

*Leaf length.*—Approximately between 117.0 and 153.0 millimeters with leaf petiole. The medium length is 136.6 millimeters.

Leaf width.—Approximately between 37.0 and 45.0 millimeters. The medium length is 40.6 millimeters.

*Leaf base shape.*—Concave.

*Leaf form.*—Lanceolate.

*Leaf tip form.*—Acuminate, short and pointed.

*Leaf color.*—

*Upper leaf surface.*—Green (RHS Yellow Green 147 A).

*Lower surface.*—A lighter green (RHS Yellow Green 147 B) than the upper leaf surface color.

*Leaf texture.*—Smooth and glabrous on both surfaces.

*Leaf venation.*—Pinnately veined.

*Mid-vein.*—

*Color.*—The mid-vein is light green almost yellow (RHS Yellow Green 150 D). The color may evolve with maturity.

*Leaf margins.*—Slightly dentate, and the margins are slightly undulating.

*Uniformity.*—Leaves are isolated or grouped by 2 or 3. In this last case, one leaf of normal size is found with one or two smaller leaves (at least 50% smaller).

*Leaf petioles.*—

*Size.*—Considered medium to small.

*Length.*—About 8.0 to about 10.0 millimeters.

*Diameter.*—About 2.0 millimeters.

*Petiole color.*—

*Upper petiole surface.*—Green (RHS Yellow Green 144 B).

*Lower surface.*—Light green (RHS Yellow Green 145 B).

*Leaf glands.*—

*Size.*—Considered small. Their length is about 1.5 millimeters and their width is about 1.0 millimeter.

*Number.*—Generally 2 glands per leaf.

*Type.*—Round.

*Color.*—On young leaves, leaf glands color is considered a light green (RHS Green 144 B to RHS Green 144 A). On older leaves, leaf glands color turns to a brown color (RHS Grey Brown 199 A to RHS Grey Brown 199 B).

*Margins.*—Smooth and regular.

*Leaf stipules.*—

*Generally.*—No leaf stipules were observed. But as seen in the characteristic relative to the leaves uniformity, it is possible to find leaves by groups of 2 or 3, with a normal-size leaf and smaller ones.

Flowers:

*Flower buds.*—

*Generally.*—At pre-floral stage of development, the floral buds are round in form with a round tip. Their form is evolving until blooming, with variables dimensions. Just before blooming, floral buds are approximately 9.0 to 9.5 millimeters wide and approximately 18.0 to 22.0 millimeters long. The distribution of the flower buds is considered homogenous on the trees.

*Color.*—This characteristic is dependent upon the proximity to bloom. At pre-floral stage of development (stage A), the bottom of the flower buds, or calyx, or flower receptacle, is of purple brown color at the outer surface of the calyx (RHS Greyed Red 178 A). The inner surface of the calyx is considered orange (RHS Yellow Orange 23 A).

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins during the first two weeks in March. The first bloom was observed on Mar. 12, 2016.

*Blooming time.*—Considered medium-season in relative comparison to other commercial nectarine cultivars grown in the Pyrénées-Orientales departement, France. The date of full bloom is observed at the middle of the blooming period. The date of bloom varies slightly with climatic conditions and cultural practices. Thus, the first full bloom was observed from Mar. 12 until Mar. 20, 2016, then from Mar. 7 until Mar. 14, 2017.

*Duration of bloom.*—Approximately 8 to 9 days. This characteristic varies slightly with the prevailing climatic conditions.

*Flower type.*—The variety is considered to have a showy type flower (rosette type) with a soft fragrance.

*Flower size.*—Considered medium to large. Flower diameter at full bloom is approximately 40.0 to 45.0 millimeters.

*Bloom quantity.*—Considered abundant, approximately between 35 and 40 flowers per meter, with a good distribution and a high rate of fruit set.

*Flower bud frequency.*—Generally 2 flower buds appear per node, occasionally 1.

*Petal size.*—

*Generally.*—Considered medium to large.

*Length.*—Generally between 20.0 to 22.0 millimeters.

*Width.*—Generally 19.0 to 21.0 millimeters.

*Petal form.*—Round-shaped.

*Petal count.*—Generally 5.

*Petal texture.*—Smooth.

*Arrangements of petals.*—Intermediate.

*Petal color.*—Both surfaces of the petal are colored in pale pink (RHS Red 56 C) when young, usually becoming slightly darker until the end of blooming.

*Fragrance.*—Soft.

*Petal claw.*—

*Form.*—The claw is considered to have a narrow shape.

*Length.*—Approximately 1.0 to 1.5 millimeters.

*Width.*—Approximately 1.5 millimeters at the base.

*Color.*—A darker pink (RHS Red Purple 63 A) than the petal color.

*Petal margins.*—Generally considered slightly undulating.

*Petal apex.*—

*Generally.*—The petal apices are generally wide-dome shaped.

*Flower pedicel.*—

*Length.*—Considered medium and having an average length of approximately 3.0 to 4.0 millimeters.

*Diameter.*—Considered average, approximately 1.0 to 1.5 millimeters.

*Color.*—Green (RHS Yellow Green 144 A).

*Calyx.*—

*Internal surface texture.*—Smooth.

*Color.*—At the stage F of blooming, when the flower is open, the inner surface of the calyx, or flower receptacle, is matt and considered orange (RHS Yellow Orange 23 A). The outer surface of the calyx is considered of purple brown color (RHS Greyed Red 178 A).

*Sepals.*—

*Number.*—Generally five sepals.

*Shape.*—Conic with a round tip.

*Surface texture.*—The outer surface has a short, fine pubescent texture.

*Margins.*—Smooth.

*Size.*—Medium to large.

*Length.*—Approximately 6.0 to 7.0 millimeters.

*Width.*—Approximately 5.0 to 6.0 millimeters.

*Color.*—At the stage F of blooming, the lower surface of the sepals is green (RHS Yellow Green 146 A to RHS Yellow Green 146 B). The upper surface of sepals is colored in purple (RHS Greyed Purple 183 A).

*Average number of stamens per flower.*—Approximately 35 to 40 stamens per flower.

*Anthers.*—

*Generally.*—Medium in length, with a cordate shape.

*Color.*—The color of the anthers evolves from a red color (RHS Orange Red N34 A) to a yellow color (RHS Yellow Orange 20 A) with maturity.

*Pollen production.*—Pollen production is considered important and the pollen shows a yellow color (RHS Yellow Orange 14 B or RHS Yellow Orange 14 C) which may evolve with maturity. The present variety is considered auto-fertile (self-pollinating).

*Filaments.*—

*Size.*—Medium length, between 16.0 and 19.0 millimeters in length. Filaments length is generally equal to the pistil's length, or higher than the pistil's length.

*Color.*—Considered white (RHS White 155 D) or pink (RHS Red 56 A) depending on the maturity stage. The color evolves and becomes darker during the blooming.

*Position compared to petals.*—Below.

*Pistil.*—

*Number.*—Usually 1.

*Generally.*—Average in size.

*Length.*—Approximately 19.0 to 20.0 millimeters including the ovary. Generally equal or smaller than stamen length, when considered without the ovary.

*Color.*—Considered a pale green (RHS Yellow Green 154 B to RHS Yellow Green 154 C). The color may evolve during the blooming.

*Stigma.*—Approximately 1.0 millimeter in diameter, with a yellow color (RHS Yellow 5 A).

*Ovary.*—Approximately 1.5 to 2.0 millimeters in height. The diameter of the ovary is about 1.0 to 1.5 millimeters. The color is considered light green (RHS Yellow Green N144 A).

*Pubescence of the ovary.*—Absent.

Fruit:

*Maturity when described.*—Very firm in ripe conditions (shipping ripe).

*Date of first picking.*—Aug. 14, 2015.

*Date of last picking.*—The date of harvest varies slightly with the prevailing climatic conditions. The 'NSRED15273' variety has a medium to late date of picking, and a grouped maturity. The maturity is grouped within 6 to 8 days and the harvest is generally performed in two runs. Last known picking times carry on from Aug. 14 to Aug. 21, 2015, then from Aug. 17 to Aug. 24, 2016, then from Aug. 5 to Aug. 10, 2017 and them from Aug. 6 to Aug. 11, 2018.

*Size.*—

*Generally.*—Homogeneous in size. Generally size A.

*Average cheek diameter.*—Approximately 64.0 to 66.0 millimeters.

*Average axial diameter.*—Approximately 58.0 to 63.0 millimeters.

*Typical weight.*—Generally about 145.0 to 160.0 grams. This characteristic is high dependent upon the prevailing cultural practices, and therefore is not particularly distinctive of the variety.

*Firmness.*—Very firm at ripening time.

*Fruit form.*—

*Generally.*—Round to slightly oblong. The fruit is symmetric in view of the suture plan.

*Fruit suture.*—Wide-mouthed and slightly marked, extending from the base to the apex. No apparent callousing or stitching exists along the suture line. Not pointed.

*Mucron.*—Absent.

*Suture.*—

*Color.*—The suture has generally a similar purple red color to the whole fruit color (RHS Greyed Purple 187 A to RHS Greyed Purple N 186 C).

*Ventral surface.*—

*Form.*—Smooth.

*Apex.*—Non-prominent, generally slightly depressed.

*Base.*—Semi-flared, shallow.

*Stem cavity.*—Flared. The depth of the stem cavity is considered medium, between 11.0 and 13.0 millimeters. Average width is about 17.0 to 19.0 millimeters.

*Fruit skin.*—

*Thickness.*—Considered very thick and strong, and the adherence of skin to flesh is strong to medium, depending on the fruit maturity.

*Texture.*—Smooth and glabrous, without any pubescence, and with few bumps.

*Taste.*—Semi-sweet, sugary and aromatic.

*Tendency to crack.*—None observed.

*Color.*—

*Blush color.*—This blush color is a dark purple red (RHS Greyed Purple 187 A to RHS Greyed Purple N 186 C). The red blush covers 95 to 100% of the fruit skin surface on a purple red (RHS Greyed Purple 185 A) background. The percentage of the blush on the fruit skin surface can vary and is generally dependant upon the prevailing conditions under which the fruit was grown.

*Ground color.*—The ground color covers at the most 5% of the fruit skin surface, and is considered purple red (RHS Greyed Purple 185A).

*Fruit stem.*—Medium in length, approximately 8.0 to 9.0 millimeters.

*Diameter.*—Approximately 4.0 millimeters.

*Color.*—Pale green (RHS Yellow Green 145 A).

*Flesh.*—

*Ripens.*—Very homogenously, slowly. The flesh has a long shelf life.

*Texture.*—Very firm, very dense, crunchy, melting, juicy at harvest maturity stage.

*Fibers.*—Not fibrous.

*Aroma.*—Pronounced.

*Eating quality.*—Considered very good and aromatic.

*Flavor*.—Considered semi-sweet, sugary and very aromatic. The Brix is generally superior to 13 and acidity is considered low and comprised between 6 and 9 meq/100 ml.

*Juice*.—Very juicy at complete maturity.

*Brix*.—Generally 16.5 to 18.5 degrees. This characteristic varies slightly with the number of fruit per tree; prevailing cultural practices; and the surrounding climatic conditions.

*Flesh color*.—The flesh of the new variety 'NSRED15273' is colored in a pink red (RHS Red 53 A) color, also named blood red color. Usually, the color is generally darker into the stone cavity.

Stone:

*Type*.—Clingstone, more or less adherent depending on the fruit maturity.

*Size*.—Considered medium for the variety. The stone size varies significantly depending upon the tree vigor, crop load and prevailing growing conditions.

*Length*.—Approximately 28.0 to 32.0 millimeters.

*Width*.—Approximately 21.0 to 23.0 millimeters.

*Diameter*.—Approximately 14.0 to 16.0 millimeters.

*Form*.—Elliptic.

*Base*.—Straight.

*Apex*.—

*Shape*.—The stone apex is short and pointed.

*Stone cavity*.—Considered medium size, with a form and dimensions corresponding to the stone's dimensions.

*Stone surface*.—

*Surface texture*.—The pit is transversely furrowed on its entire surface. Furrows are more pronounced toward the apex. The stone is pitted toward the base. Relief is prominent generally and present basally.

*Ridges*.—The surface texture is generally characterized by more prominent ridges along the ventral edges and is more prominent at the apical tip.

*Ventral edge*.—

*Width*.—Considered small, and having a dimension of approximately 1.5 millimeters at mid-suture.

*Dorsal edge*.—

*Shape*.—Grooved.

*Stone color*.—The color of the dry stone is generally considered light brown (RHS Greyed Orange 165 C to RHS Greyed Orange 165 D).

*Tendency to split*.—Splitting is absent or very low, depending on climatic conditions between blooming period and stone hardening.

*Kernel*.—

*Size*.—The kernel is considered medium.

*Length*.—Approximately 14.0 to 15.0 millimeters.

*Width*.—Approximately 10.0 to 11.0 millimeters.

*Thickness*.—Approximately 4.0 to 5.0 millimeters.

*Form*.—Elliptic and flattened.

*Pellicle*.—The pellicle of the kernel has a short pubescence.

*Taste*.—Bitter.

*Color*.—The kernel skin is a light brown color (RHS Greyed Orange N167 A). The almond, which is the seed of the kernel, is white (RHS White 155 D). The kernel and its embryo are mature at the time of fruit maturity.

*Use*.—The subject variety 'NSRED15273' is considered to be a nectarine tree having a late season of fruit maturity, and which produces fruits that are considered firm, attractively colored with a very dark purple red. The high content of antioxidant in the red flesh convert fruits in a very healthy product. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.

*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

*Shipping quality*.—Considered very good. The fruit of the new red blood nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to insects and disease*.—No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orienteles departement, France, it should be understood that variations of the usual magnitude and characteristics incident to changes in growing conditions, fertilization, pruning, pest control and horticultural management are to be expected.

We claim:

1. A new and distinct variety of red blood nectarine tree as illustrated and described, characterized by fruits with high eating quality and very long shelf life without alteration before and after harvesting, with a semi-sweet pink red blood colored flesh, and a very high percentage of purple red blush on skin surface.

* * * * *